US009885005B2

(12) United States Patent
Kaji et al.

(10) Patent No.: US 9,885,005 B2
(45) Date of Patent: Feb. 6, 2018

(54) PHOSPHOLIPID ALPHA-LINOLENIC ACID COMPOSITION

(71) Applicants: KOHJIN LIFE SCIENCES CO., LTD., Tokyo (JP); HIROSAKI UNIVERSITY, Aomori (JP)

(72) Inventors: Naoto Kaji, Oita (JP); Shiroh Aida, Oita (JP); Katsuhiro Osaki, Oita (JP); Masato Omae, Oita (JP); Tomohiro Nakagawa, Oita (JP); Motoyuki Tokuriki, Oita (JP); Hayato Maeda, Aomori (JP)

(73) Assignees: KOHJIN LIFE SCIENCES CO., LTD., Tokyo (JP); HIROSAKI UNIVERSITY, Aomori (JP)

( * ) Notice: Subject to any disclaimer, the term of this patent is extended or adjusted under 35 U.S.C. 154(b) by 0 days.

(21) Appl. No.: 15/126,793

(22) PCT Filed: Mar. 9, 2015

(86) PCT No.: PCT/JP2015/056804
§ 371 (c)(1),
(2) Date: Sep. 16, 2016

(87) PCT Pub. No.: WO2015/141507
PCT Pub. Date: Sep. 24, 2015

(65) Prior Publication Data
US 2017/0081610 A1    Mar. 23, 2017

(30) Foreign Application Priority Data

Mar. 17, 2014   (JP) ................. 2014-053559
Sep. 8, 2014    (JP) ................. 2014-182006

(51) Int. Cl.
*A61K 47/00*    (2006.01)
*C11B 1/02*     (2006.01)
*A23D 9/013*    (2006.01)
*A61K 31/66*    (2006.01)
*A23L 33/12*    (2016.01)
*A61K 31/661*   (2006.01)

(52) U.S. Cl.
CPC .............. *C11B 1/025* (2013.01); *A23D 9/013* (2013.01); *A23L 33/12* (2016.08); *A61K 31/66* (2013.01); *A61K 31/661* (2013.01); *A23V 2002/00* (2013.01)

(58) Field of Classification Search
CPC ..................................... A61K 31/202
USPC ......................................... 424/439
See application file for complete search history.

(56) References Cited

U.S. PATENT DOCUMENTS

2004/0234587 A1   11/2004  Sampalis
2006/0135610 A1   6/2006   Bortz et al.
2007/0122452 A1   5/2007   Moriguchi et al.

FOREIGN PATENT DOCUMENTS

| JP | 02-053726   | 2/1990  |
| JP | 05-030981   | 2/1993  |
| JP | 2006-158340 | 6/2006  |
| JP | 2006-311853 | 11/2006 |
| JP | 2008-525441 | 7/2008  |
| WO | 2005/061684 | 7/2005  |
| WO | 2006/071342 | 7/2006  |

OTHER PUBLICATIONS

YoshihiroMurano et al., "Effect of Dietary Lard Containing Higher α-Linolenic Acid on Plasma Triacylglycerol in Rats"; Journal of Oleo Science (J. Oleo Sci), 56; Mar. 5, 2007, pp. 361-367.
StephanWinnik et al."Dierary α-linolenic acid diminishes experimental atherogenesis and restricts T cell-driven inflammation"; European Heart Journal (Eur Heart J), No. 32; Jan. 31, 2011; pp. 2573-2584.
Hisashi Yazawa et al.; "Porduction of polyunsaturated fatty acids in yeast Saccharomyces cerevisiae and its relation to alkaline pH tolerance"; Yeast, No. 26; 2009, pp. 167-184.
Yukihiro Yamamoto et al., "Preparation of functional phospholipids mediated by enzymatic acidolysis", The Journal of the Faculty of Science and Technology, Seikei University, Rikogakubu/Kogakubu Kaisetsu 50 Shunen Kinengo, vol. 49, No. 2; Dec. 1, 2012; pp. 95-96.
A. Chojnacka et al., "Enzymatic enrichment of egg yolk phospatidylcholine with α-linolenic acid"; Biotechnology Letters, vol. 31, No. 5; May 2009; pp. 705-709.
Takashi Negishi et al.; "Chemical Composition of the Phospholipids prepared from commercial 'Soy bean lecithin'"; Research bulletin of Obihiro Zootechnical University. Series I, vol. 5, No. 1: Mar. 31, 1967, pp. 97-101.
Setsuko Hara et al., "Novel fractionation method for soy phospholipid classes", The Journal of the Faculty of Science and Technology, Seikei University, vol. 44, No. 2; Dec. 2007, pp. 65-73.
C.R. Scholfield, "Composition of Soybean Lecithin "; Journal of the American Oil Chemists' Society, vol. 58, No. 10; Oct. 1981, pp. 889-892.
Jae Won Lee et al., "Simultaneous profiling of polar lipids by supercritical fluidchromatography/tandem mass spectrometry with methylation", Journal of Chromatography A, vol. 1279: Mar. 1, 2013, pp. 98-107.
Shota Doguro et al., "α-linolenic Acid Ko Gan'yu Phospholipid ni yoru Shokujisei Himan Kaizen Sayo", Japan Oil Chemists' Society Dai 53 Kai Nenkai Koen Yoshishu; Sep. 9, 2014, pp. 82.
International Search Report issued in PCT/JP2015/056804, dated Sep. 8, 2015.

*Primary Examiner* — Jeffrey H Murray
(74) *Attorney, Agent, or Firm* — Greenblum & Bernstein, P.L.C.

(57) ABSTRACT

[Problem] To provide a phospholipid α-linolenic acid composition of consistent quality and having a stable supply of source material, with focus on Torula yeast, which is edible and recognized as safe, in order to resolve issues with omega 3 sources.
[Means for Solving the Problem] As a result of intensive study to resolve the above-noted issues, the inventors of the present invention have discovered that a phospholipid α-linolenic acid composition can be obtained using residue of yeast extract extracted from Torula yeast (*Candida utilis*), for example, which is currently produced in large quantities for application in foods, and so arrived at the present invention.

7 Claims, 3 Drawing Sheets

PHOSPHOLIPID ALPHA-LINOLENIC ACID COMPOSITION

FIELD OF THE INVENTION

The present invention relates to a composition containing a phospholipid α-linolenic acid. The invention particularly relates to a phospholipid composition which is effective as a functional food or a medicinal product. More specifically, the present invention relates to a composition containing a high concentration of bonded α-linolenic acid (as a fatty acid residue) derived from a source containing α-linolenic acid.

BACKGROUND OF THE INVENTION

Phospholipids have excellent amphiphilic and biocompatibility properties, and are used for a wide variety of purposes ranging from functional foods to medicinal products. Representative phospholipids include phosphatidyl choline (PC), phosphatidyl ethanolamine (PE), phosphatidyl inositol (PI), and phosphatidyl serine (PS). The phospholipid is used in a food additive as a lecithin-like emulsifier, and in a medicinal product as a liposome.

In recent years, awareness of omega 3 fatty acids (EPA, DHA, α-linolenic acid) has incrementally increased in Japan. α-linolenic acid is an omega 3 fatty acid which is a precursor of EPA and DHA, and has been reported (Non-Patent Literature 1, Non-Patent Literature 2) to have bioactive properties such as anti-inflammatory effects and improving cardiovascular diseases (lowering blood lipid). Cardiovascular diseases, in particular, comprise one of the three major diseases in Japan, Europe, and America, and improvement of these disorders is critical.

Exemplary sources of omega 3 fatty acids include fish, algae, linseed, and the like. In fish and algae, EPA and DHA are the primary fatty acids, whereas in linseed, α-linolenic acid is the primary fatty acid.

In particular, phospholipid-type omega 3 fatty acids are reported to have a greater effect of improving liver function, reproductive function, and brain function than ordinary triglyceride-types, and have therefore attracted attention. Exemplary sources of phospholipid-type omega 3 include krill oil, fish eggs (such as salmon), and fishery waste products. In particular, krill oil sourced from Antarctic krill is available for sale. A phospholipid omega 3 fatty acid composition derived from Antarctic krill (hill oil) has a phospholipid concentration of approximately 40% (W/W composition), and includes high-concentration triglycerides (approximately 45%) and free fatty acids (approximately 15%) (Patent Literature 1). In addition, a method has been reported of manufacturing a useful phospholipid derived from seafood, and in particular from waste products created in processing seafood (Patent Literature 2). However, when using marine products as a source, there is anxiety about heavy metals, arsenic, and the like due to oceanic pollution. Moreover, there is caution due to an instability in catch and phospholipid content due to seasonal changes. Therefore, an alternative source is sought which is unlikely to be subject to seasonal changes and which is capable of high quality, stable production. Furthermore, because lipids derived from krill oil, seafood, and the waste products thereof have phospholipid EPA and DHA as primary components, sources having phospholipid α-linolenic acid as a primary component are more preferred.

As noted above, linseed oil contains α-linolenic acid, but it is of a triglyceride type rather than a phospholipid-bound type. There are examples of attempting to prepare phospholipid α-linolenic acid from linseed oil rich in triglyceride α-linolenic acid by transesterification with an enzyme (Non-Patent Literature 3). However, because this method uses an enzyme or the like, the method requires complex operations and can potentially increase costs. Lecithin sourced from soybeans or egg yolk is common, but linoleic acid is the primary fatty acid and there is at most 10% α-linolenic acid, which is insufficient. As a dairy source, a method is given to increase phospholipid content from milk using a microfilter membrane (Patent Literature 3). However, this does not focus on increasing the content of phospholipid α-linolenic acid. In addition, using yeast as a source, a method is known of extracting fats such as linoleic acid from prototypical baker's yeast or brewer's yeast using hexane (Patent Literature 4). However, baker's yeast is known to be incapable of accumulating α-linolenic acid (Non-Patent Literature 4), and extracting phospholipids with hexane is difficult. Accordingly, there is no composition known to date which is capable of containing a large amount of phospholipid α-linolenic acid.

RELATED ART

Patent Literature

Patent Literature 1: U.S. Patent Publication No. 2004/0234587 (Specification)
Patent Literature 2: Japanese Patent Laid-open Publication No. 2006-311853 (Publication)
Patent Literature 3: Japanese Patent Laid-open Publication No. 2006-158340 (Publication)
Patent Literature 4: Japanese Patent Laid-open Publication No. H05-030981 (Publication)

Non-Patent Literature

Non-Patent Literature 1: "Journal of Oleo Science" (J. Oleo Sci) 2007, no. 56, p. 361-367
Non-Patent Literature 2: "European Heart Journal (Eur Heart J)" 2011, no. 32, p. 2573-2584
Non-Patent Literature 3: "Seikei University Faculty of Science and Technology Research Report" 2012, p. 95-96
Non-Patent Literature 4: "Yeast" 2009, no. 26, p. 167-184

SUMMARY OF THE INVENTION

Problems to be Solved by the Invention

In order to resolve the above-noted issues with sources of phospholipid omega 3s, Torula yeast, which is edible and is considered to be safe, is to be investigated and a highly pure phospholipid α-linolenic acid of good and stable quality and having a ready, stable source supply is to be provided.

Means for Solving the Problems

As a result of intensive studies with the objective of resolving the aforementioned problems, the inventors arrived at the present invention by finding that a phospholipid α-linolenic acid composition could be obtained using a yeast residue as a source in alcohol extraction, the yeast residue being obtained after extraction of yeast extract from Torula yeast (*Candida utilis*) or the like, which is currently mass produced for food applications.

The present invention provides:
  (1) A functional food containing phospholipid α-linolenic acid extracted from a yeast residue after extraction of yeast extract;

(2) A medicinal product containing phospholipid α-linolenic acid extracted from a yeast residue after extraction of yeast extract; and
(3) A manufacturing method extracting phospholipid α-linolenic acid extracted from a yeast residue after extraction of yeast extract.

These useful phospholipid compositions include at least 30 mass % phospholipid content. According to the above configuration, a composition rich in phosphatidyl choline PC can be obtained.

Specifically provided are:
(1) A composition containing phospholipid α-linolenic acid extracted from yeast, the composition including a chemical compound according to general formula (1), the chemical compound according to general formula (1) having a content of at least 30 mass % of the phospholipid α-linolenic acid composition.

[Chemical Formula 1]

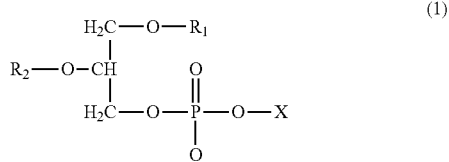

(1)

(In general formula (1), R1 is selected from hydrogen or a desired fatty acid; R2 is selected from hydrogen or a desired fatty acid; at least one of R1 and R2 is a fatty acid; and X is one selected from choline residue (PC), ethanolamine residue (PE), inositol residue (PI), and serine residue (PS).)

(2) The composition according to (1) where phosphatidyl choline (PC), which includes the choline residue, is at least 50 mass % (PC/total phospholipid) of the chemical compound according to general formula (1).
(3) The composition according to (1) where R1 and R2 are each independent α-linolenic acids.
(4) The composition according to (1) where R1 is α-linolenic acid.
(5) The composition according to (1) where R2 is α-linolenic acid.
(6) The composition according to (1) where R1 and R2 are α-linolenic acid.
(7) The composition according to (1) where α-linolenic acid, which is a fatty acid constituent in the phospholipid α-linolenic acid composition, is included as at least 30% of the total fatty acids.
(8) A functional food containing the lipid α-linolenic acid composition according to any one of (1) to (7).
(9) A medicinal product containing the lipid α-linolenic acid composition according to any one of (1) to (7).

Effect of the Invention

According to the present invention, a composition containing phospholipid α-linolenic acid can be provided from Torula yeast or the like, which is edible and known to be safe. The composition of the present invention has a less obtrusive smell than other phospholipid omega 3 sources and therefore can be used for a broad range of applications, from food and beverages to cosmetics and medicinal products. Yeast extract of Torula yeast is suitable as a flavoring agent and is mass-produced. With effective use of its residue, the present invention is a very advantageous method in view of reductions in cost and industrial waste, as well.

MODE FOR CARRYING OUT THE INVENTION

Figure 1:
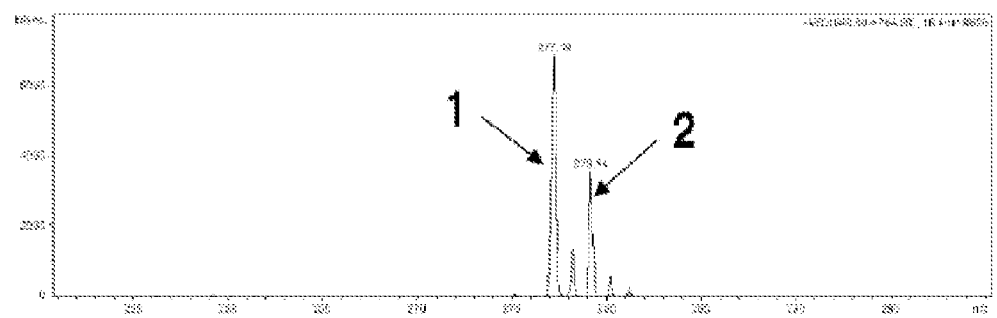
FIG. 1 is an MS3 chromatogram where Torula oil (the present invention) M/Z=840.
Figure 2:
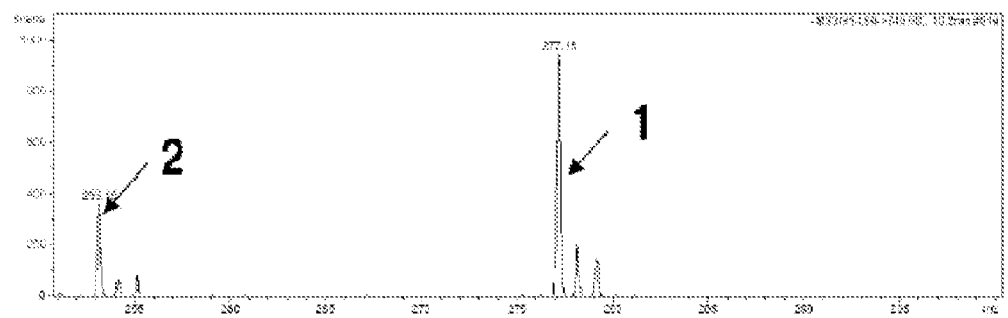
FIG. 2 is an MS3 chromatogram where Torula oil (the present invention) M/Z=814.

A phospholipid composition according to the present invention can be used as a food, functional food, or medical product. A functional food according to the instant application may refer to a health food, supplement, food having nutritive function, or the like which is expected to provide a health regulating effect by ingesting a phospholipid α-linolenic acid composition according to the present invention. However, the functional food is not limited to this.

A "fatty acid" as used in the instant specification may be saturated or unsaturated. Examples of a saturated fatty acid include, without limitation to the following, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, henicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, hentriacontanoic acid, dotriacontanoic acid, tritriacontanoic acid, tetratriacontanoic acid, pentatriacontanoic acid, hexatriacontanoic acid, and the like. An unsaturated fat may be a fat or fatty acid having one or a plurality of double bonds in a fatty acid chain. When only one double bond is present, the fat molecule is monounsaturated. When a plurality of double bonds are present, the fat molecule is polyunsaturated. Examples of unsaturated fatty acids include, without limitation to the following, myristoleic acid, palmitoleic acid, sapienic acid, oleic acid, linoleic acid, α-linolenic acid, arachidonic acid, eicosapentaenoic acid (EPA), erucic acid, docosahexaenoic acid (DHA), docosapentaenoic acid, and the like.

(Method of Manufacturing Phospholipid Composition)

*Candida utilis*, referred to as Torula yeast, is a preferred source in the present invention. However, so long as the source contains the target component, the source is not particularly limited and may include fungi, for example, such as yeasts of genus *Candida*, genus *Kluyveromyces*, and genus *Zygosaccharomyces*. A method of culturing the yeast is not particularly limited. The method of culturing the yeast is either batch culture or continuous culture. In general, examples of a carbon source in the culture medium may include glucose, acetic acid, ethanol, glycerol, molasses, and spent sulfite liquor. Examples of a nitrogen source may include urea, ammonia, ammonium sulfate, ammonium chloride, and nitrate. As sources of phosphoric acid, potassium, and magnesium, normal industrial materials may be used, including calcium superphosphate, ammonium phosphate, potassium chloride, potassium hydroxide, magnesium sulfate, and magnesium chloride. Furthermore, inorganic salts, such as zinc, manganese, and iron ions, may be added. Additionally, vitamins, amino acids, and nucleic acid-related substances may be added. Also, organic materials, such as casein, yeast extract, meat extract, and peptone, may be added.

The most preferable example of a source to be used in the present invention is yeast extract residue. In the instant application, yeast extract residue refers to solid components after yeast extract, for example, has been extracted from cultured yeast. A method of yeast extract extraction is not particularly limited. Generally, extraction can be performed with an autolysis method, a hot water extraction method, an enzymatic extraction method, an acid or alkaline extraction method, or a combination of these methods. The instant application refers to the yeast cell bodies and solid content extracted by such extraction methods as yeast extract residue. After this residue is dried with a drum dryer, phospholipid production (described below) can be performed.

A phospholipid composition derived from the above-listed sources can be manufactured or produced using any method known to one of ordinary skill in the art. For example, a manufacturing process in the present invention may include a process of extraction from the source, a water separation and cooling process, a filtration/concentration process, or a pulverization process. The process of extraction from the source and subsequent processes are not particularly limited, and can be combined as appropriate for a given objective.

The extraction process may use any one method from among organic solvent extraction, enzyme treatment followed by organic solvent extraction, and supercritical extraction. For example, in the case of the organic solvent extraction, examples of the solvent used may include methanol, ethanol, n-propanol, hexane, acetone, and a chlorinated solvent. The solvent is preferably a low-grade alcohol having 1 to 3 carbons. In a case where the extract is to be used for food, the solvent is more preferably ethanol. In the present invention, the solvent may also contain moisture ethanol, which is a mixture of water (such as distilled water) used in industry. By changing the water content ratio, an amount of phospholipid in the obtained phospholipid composition can be adjusted. Therefore, moisture ethanol corresponding to the objective may be used. A water/ethanol volume ratio is typically between 0.01/99.99 and 30/70, preferably between 0.5/99.5 and 30/70. The water content may take into consideration an amount of water in the source material, or not. The amount of ethanol used is not particularly limited. Typically, between 1 and 20 parts by mass are used, relative to the source material, and preferably between approximately 2 and 3 parts by mass. In the extraction method, after adding ethanol and stirring sufficiently, a reaction is performed at an appropriate temperature for an appropriate length of time. The temperature is not particularly limited and is typically 20° C. to less than 80° C., and is preferably between 50° C. and 70° C. The extraction time is not particularly limited and is typically at least one hour, and is preferably between 3 and 9 hours. Examples of extraction methods include agitation, reflux, dipping, shaking, and ultrasonic extraction. In a case where enzyme treatment is performed prior to extraction, the extraction time can be shortened. Examples of an enzyme include cell wall lytic enzymes such as a Streptomyces-derived β-glucanase "Denatyme GEL" (manufactured by Nagase ChemteX Corporation), a Taloromyces-derived β-glucanase "Filtrase BRX" (manufactured by DSM Japan), and "Tunicase FN" manufactured by Amano Enzyme Inc. Tunicase FN is preferred. Supercritical extraction is a method in which carbon dioxide in a supercritical state is brought into contact with a yeast suspension, after which pressure is reduced back to atmospheric pressure, thereby separating the carbon dioxide from the yeast suspension.

After performing organic solvent extraction, a separation process or cooling process in which water is added may be added to eliminate neutral lipids, ergosterol, and free fatty acids. Oxidation can thus be impeded and deterioration over time can be ameliorated. An ethanol concentration adjusted by adding water should be between 50 and 90%, and preferably should be 70%. In the cooling process, a cooling temperature should be 10° C. and below. A temperature of 5° C. and below is particularly preferred. A cooling time should be between 1 and 10 hours and, because the phospholipid begins to become insoluble over a long period of time, the cooling time should preferably be approximately one hour.

When concentration is performed, a known concentrating device can be used. A preferred example is a vacuum concentrator capable of lowering the temperature as much as possible so as to prevent the phospholipid from dissolving.

Furthermore, cyclodextrin, cluster dextrin, and the like can be added as a diluting agent in order to inhibit medium chain fatty acids and inhibit odor, and drying can be performed. Drying can be performed using a known drying method such as freeze-drying, vacuum drying, and the like.

Purity of the composition according to the present invention can be increased with a silica gel column or the like, in accordance with a required degree of purity, an odor from the source material, or the like. Any of the processes described above can be combined as appropriate.

With the composition according to the present invention, as described above, a phospholipid omega 3 composition can be obtained from yeast or yeast extract residue. In addition, by combining the processes detailed in the instant specification, the phospholipid linolenic acid composition according to the present invention can be obtained which includes at least 30 mass % of the chemical compound according to general formula (1), and moreover, of the chemical compound according to general formula (1), phosphatidyl choline (PC) having choline residue constitutes at least 50 mass % of the phospholipids (PC/total phospholipids) and α-linolenic acid constitutes at least 30 mass % of the total fatty acids.

The composition according to the present invention can be used singly or in combination with other components as a food or beverage. Forms such use as a food or beverage might take include any food form, such as solid foods, gel foods, or the like. Examples may include forms such as a powder, capsule, granule, tablet, or the like. A capsule, which is readily produced and has high oxidation prevention properties, is preferred. Such foods or beverages can be produced in accordance with typical methods.

In addition, the composition according to the present invention can take the form of a medicinal product by adding a carrier permissible in pharmaceutical preparations. The form of the medicinal product is not particularly limited and may include, for example, a capsule, a tablet, a pill, a lozenge, a powder, and a granule. A capsule, which is readily manufactured, is preferred.

The phospholipid can be analyzed with a known method. After extracting a sample using the Folch method, the sample was submitted to thin layer chromatography using two-dimensional development. Conditions included using a silica gel on a thin film plate, using tetrahydrofuran:acetone: methanol and water 50:2:40:8 as a one-dimensional development solvent, and using chloroform:acetone:methanol: acetate and water (50:20:10:15:5) as a two-dimensional development solvent. Dittmer spray reagent was used as the color development method. After development, portions corresponding to each phospholipid were individually scraped off, were subjected to wet decomposition, and a colorimetric determination was made using molybdenum blue absorption photometry.

The fatty acid constituents of the composition were analyzed using gas chromatography (Tsushima model GC-14B) by boron trifluoride methyl esterification of structural fatty acids. A Fused Silica Capillary Column Omegawax 320 (30 m×0.32 mm i.d.) [Supelco Inc., Bellefonte, Pa., USA] was used as a column, helium was used as a carrier gas, and detection was performed with flame ionization detection (FID).

Liquid chromatography/mass spectrometry (LC/MS) was performed for a structure of the composition. An Inertsil SIL 100A (4.6×100 mm, manufactured by GL Sciences, 3 μm) was used as the column, and chloroform and a gradient of methanol:water=95:5 (capacity ratio) were used as a dissolution medium. Column temperature was 35° C. and flow rate is 1 ml/min. An electrospray ionization device (ESI, manufactured by amaZon SLTM Bruker Daltonics K.K.) is used in the detection. Nitrogen was allowed to flow at a rate of 12 L/min, the temperature was raised to 250° C. for desolventizing, and nebulizer gas was allowed to flow at a pressure of 45 psi. Measurement was conducted in a negative mode, and capillary electric potential was set to 4.5 kV while end plate offset was set to 0.5 kV. Mass spectrometry was conducted in a range of 200 to 900 m/z. Multistage mass spectrometry up to MS3 was conducted.

The present invention is described in detail below with reference to embodiments. However, the technical scope of the present invention is not limited in any respect to these descriptions. The following examples are carried out according to common methods known to one of ordinary skill in the art, unless such methods are expressly prohibited.

Exemplary Manufacture 1
(Culture of Yeast)

*Candida utilis* CS 7529 strain (FERMP-3340) was seed-cultured in advance in a YPD culture medium (1% yeast extract, 2% polypeptone, 2% glucose) in a conical flask, and then 1 to 2% thereof was inoculated in an 18 L culture medium in a 30 L fermentation tank. A culture medium composition was 4% glucose, 0.3% ammonium dihydrogentetraoxophosphate, 0.161% ammonium sulfate, 0.137% potassium chloride, 0.08% magnesium sulfate, 1.6 ppm copper sulfate, 14 ppm iron sulfate, 16 ppm manganese sulfate, and 14 ppm zinc sulfate. Culture conditions were a pH of 4.0, a culture temperature of 30° C., an aeration rate of 1 vvm, and a stirring rate of 600 rpm. Ammonia was used to control the pH. After a cell body was cultured for 16 hours, a culture solution was collected, and then the cell body was collected by centrifugal separation to yield 180 g of wet yeast cell body.

(Extraction of Yeast Extract)

The wet yeast cell body obtained after the cell body culture was suspended in distilled water and centrifugally separated repeatedly for cleaning. After cleaning, the wet yeast cell body is once again suspended in distilled water, or a dried yeast cell body that has been freeze-dried or hot air-dried is suspended in distilled water. The pH was controlled to 13 with 2N NaOH, and then stirring was performed for 20 minutes at a temperature of 70° C. and the yeast extract was extracted. The yeast cell body residue after the yeast extract has been extracted was dried in a drum dryer and 100 g of the dried product was used as a source material. Phosphatidyl choline content of the dried product was 2.8%.

Embodiment 1

Extraction was performed on 100 g of the source material described above with 95% ethanol at 60° C. for 9 hours. Water was added to the extraction liquid to achieve an ethanol concentration of 70% and the temperature was brought to 5° C. This was maintained for one hour, after which filtration was performed with filtration paper (ADVANTEC Co., No. 5C) to remove insolubles. The filtrate was then vacuum concentrated and desiccated in a rotary evaporator and 5.5 g of the composition was obtained. Residual ethanol concentration in the desiccated material was 2.5%. Phospholipid content of the composition was 71.7% and phosphatidyl choline content was 48%. Fatty acid constituents of the phospholipid composition included α-linolenic acid at 38%, linoleic acid at 29%, oleic acid at 15%, and palmitoleic acid at 4.2%.

Embodiment 2

Extraction was performed on 100 g of the source material described above with 95% ethanol at 60° C. for 9 hours. Water was added to the extraction liquid (phosphatidyl choline content of at least 40%) to achieve an ethanol concentration of 70% and the temperature was brought to 5° C. This was maintained for one hour, after which filtration was performed with filtration paper (ADVANTEC Co., No. 5C) to remove insolubles. The filtrate was then vacuum concentrated and desiccated in a rotary evaporator. After 5.5 g of the desiccated material was dissolved in ethanol, this was applied to a silica gel column (volume 100 mL, FL60BD, Fuji Silysia Chemical Ltd.) and the column was dipped in 95% ethanol. A fraction containing phosphatidyl choline is separated out and concentrated once again to obtain 3 g of composition. Phospholipid content of the composition was 95% and phosphatidyl choline content was 88.3%. Fatty acid constituents of the phospholipid composition included α-linolenic acid at 46%, linoleic acid at 26%, oleic acid at 11%, and palmitoleic acid at 7.7%.

The drawings show an LC-MS multistage MS3 fragment pattern of the phospholipid-bound α-linolenic acid composition prepared according to Embodiment 2. There are primarily two types of phospholipid, whose M/Z is 840 and 814, respectively. In the type having molecules where M/Z=840, the fatty acids bonded to the phospholipid are α-linolenic acid and linoleic acid. In the type having molecules where M/Z=814, the fatty acids bonded to the phospholipid are α-linolenic acid and palmitoleic acid.

Embodiment 3

Figure 3:
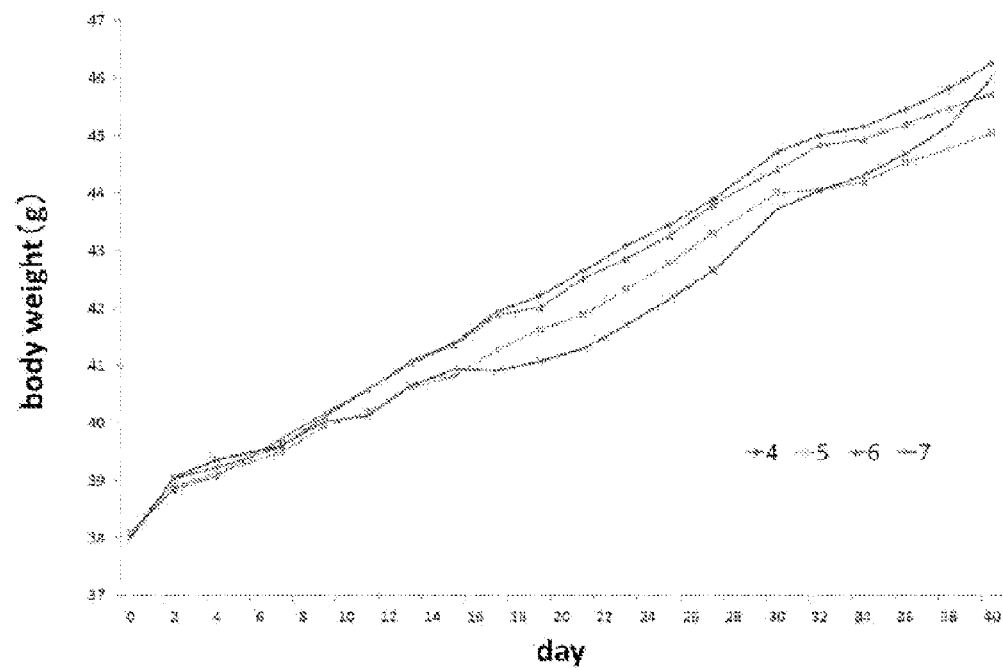
FIG. 3 is a change in body weight (Embodiment 3).
Figure 4:
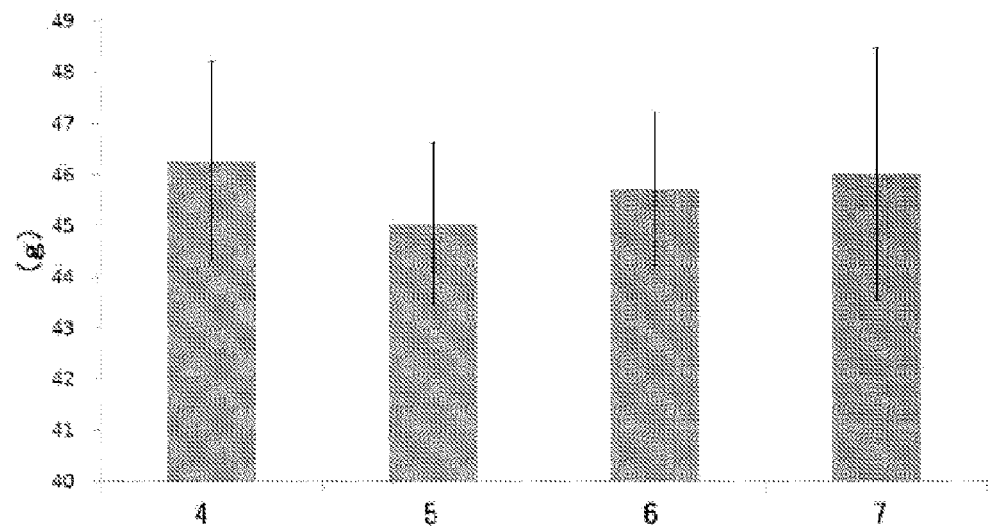
FIG. 4 is a body weight comparison after forty days (Embodiment 3).
Figure 5:
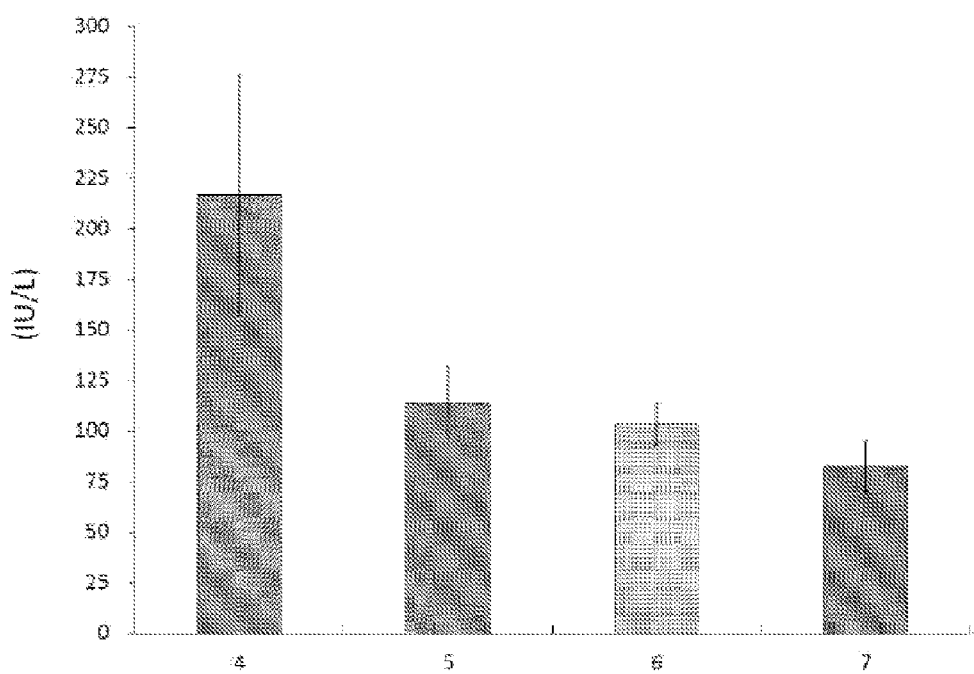
FIG. 5 illustrates biochemical analysis results of blood (GOT) (Embodiment 3).
Figure 6:
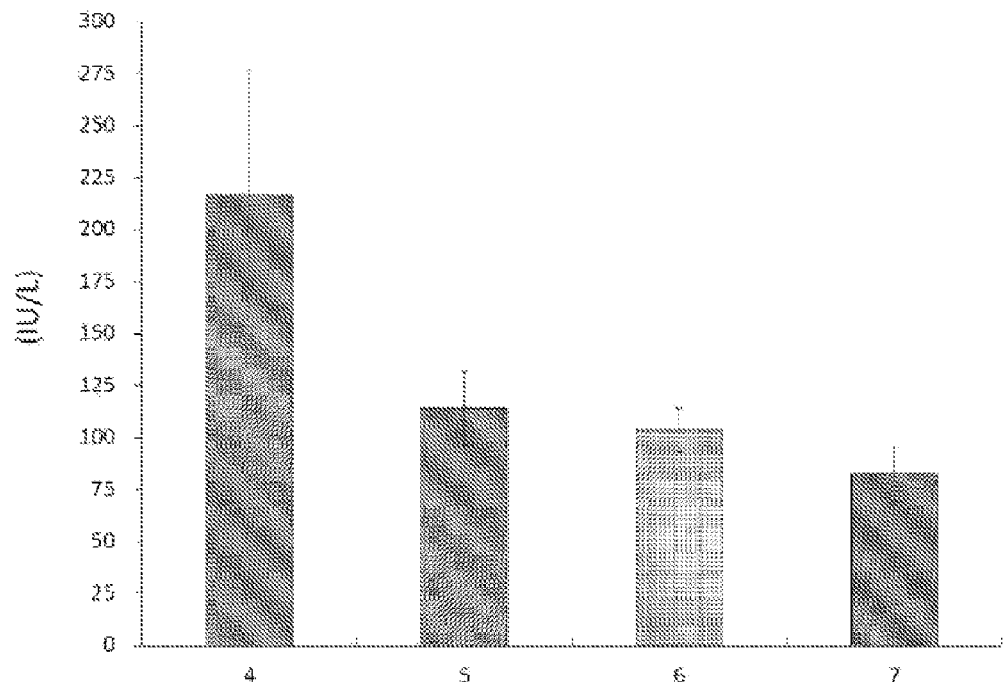
FIG. 6 illustrates biochemical analysis results of blood (GPT) (Embodiment 3).
Figure 7:
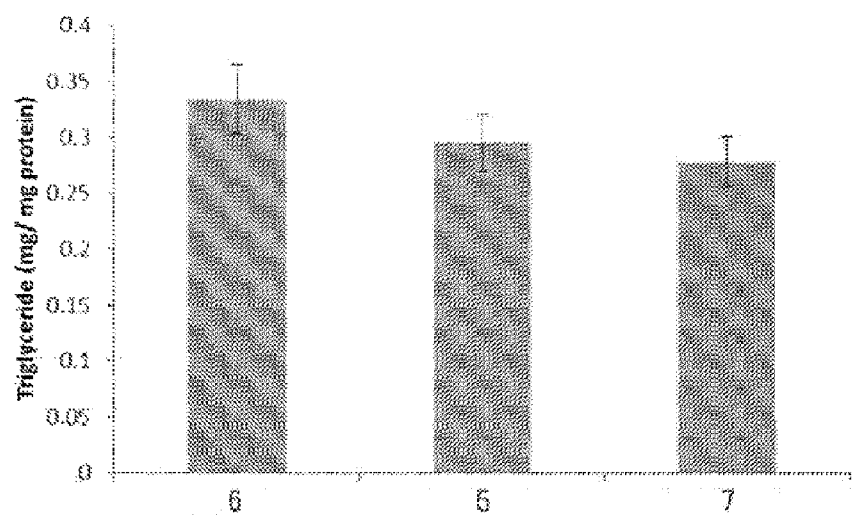
FIG. 7 illustrates triglyceride concentration in the liver (Embodiment 3).

Feed having a sample fat added at 2% to a high-fat food (20% fats) was given to mice (C57BL/6J mouse, three week-old males reared for two weeks in preparation) were given the composition of the instant application obtained in Embodiment 2 and linseed oil (product name "Linseed Oil, mfd. by Wako Pure Chemical Industries, Ltd.") and krill oil (product name "Koyo Krill Oil" mfd. by Koyo Chemical Co., Ltd.), and animal testing of liver function and fat metabolism improvement was conducted. After seven weeks, the mice were dissected and effects on plasma lipid were evaluated. Changes in body weight during the seven week period were also measured. The changes in body weight are shown in FIG. 3. A weight comparison after 40 days is shown in FIG. 4. The composition of the instant application showed a trend of reduction in weight greater than that of other compositions after 40 days. Results of biochemical analysis of blood, GOT (AST) values, and GPT (ALT) values showed a similar reduction (FIG. 5) for the composition of the instant application (5), linseed oil (6), and krill oil (7) as compared to a control (4). (FIGS. 5 and 6) Moreover, the composition of the instant application exhibited a low value for triglyceride concentration in the liver, close to that of krill oil (FIG. 7).

The phospholipid-bound α-linolenic acid composition according to the present invention is obtained from yeast or yeast extract residue and therefore has a mild odor. Accordingly, the composition can be favorably used in foodstuffs and can also be used as a medicinal product. Absorption is also good compared to other phospholipid-bound α-linolenic acid compositions. Furthermore, the yeast residue-derived phospholipid-bound α-linolenic acid composition of the instant application has excellent effects similar to other phospholipid-bound α-linolenic acid compositions not derived from yeast, such as reduction of neutral lipids and free fatty acids, reduction of blood sugar levels, and the like. In addition, due to the reduction of GPT (ALT) values, the composition according to the present invention can be used as a medicinal product or foodstuff treating, preventing, and improving non-alcoholic lipid disorders.

DESCRIPTION OF REFERENCE NUMERALS

1 α-linolenic acid (C18:3)
2 Linoleic acid (C18:2)
3 Palmitoleic acid (C16:1)
4 Control
5 Composition of the instant application
6 Linseed oil
7 Krill oil

The invention claimed is:

1. A composition containing phospholipid α-linolenic acid extracted from yeast, the composition including a chemical compound according to general formula (1), the chemical compound according to general formula (1) having a content of at least 30 mass % of the phospholipid α-linolenic acid composition

[Chemical Formula 1]

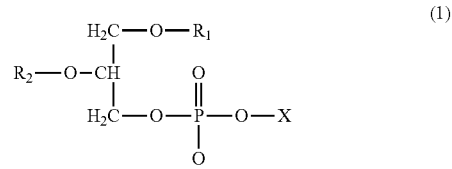

(1)

In general formula (1), R1 is selected from hydrogen or a desired fatty acid;
R2 is selected from hydrogen or a desired fatty acid;
at least one of R1 and R2 is a fatty acid; and
X is one selected from choline residue (PC), ethanolamine residue (PE), inositol D residue (PI), and serine residue (PS).

2. The composition according to claim 1, wherein phosphatidyl choline (PC), which includes the choline residue, is at least 50 mass % (PC/total phospholipid) of the chemical compound according to general formula (1).

3. The composition according to claim 1, wherein R1 and R2 are each independent α-linolenic acids.

4. The composition according to claim 1, wherein R1 is α-linolenic acid.

5. The composition according to claim 1, wherein R2 is α-linolenic acid.

6. The composition according to claim 1, wherein R1 and R2 are α-linolenic acid.

7. The composition according to claim 1, wherein α-linolenic acid, which is a fatty acid constituent in the phospholipid α-linolenic acid composition, is included as at least 30% of the total fatty acids.

* * * * *